United States Patent [19]

Riley et al.

[11] Patent Number: 4,755,208
[45] Date of Patent: Jul. 5, 1988

[54] BIOLOGICAL CONTROL OF WILD POINSETTIA AND OTHER WEEDY SPURGES WITH A FUNGAL PATHOGEN

[75] Inventors: Joe A. Riley; Harrell L. Walker, both of Ruston, La.

[73] Assignee: Mycogen Corporation, San Diego, Calif.

[21] Appl. No.: 856,614

[22] Filed: Apr. 25, 1986

[51] Int. Cl.$^4$ ............................................. A01N 63/00
[52] U.S. Cl. ......................................... 71/79; 435/911
[58] Field of Search ............................ 435/911; 71/79

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,097,261 | 6/1978 | Conway et al. | 71/66 |
| 4,390,360 | 6/1983 | Walker | 71/79 |
| 4,419,120 | 12/1983 | Walker | 71/79 |

OTHER PUBLICATIONS

Simmons et al., "Alternaria Themes and Variations", Biosis 86: 187567 (Biological Abstracts) from Mycotaxon 25(1):195 (1986).
Krupinsky et al., "An *Alternaria* Sp. on Leafy Spurge (*Euphorbia esula*)", Weed Science 31: 86–88 (1983).
Akobundu, I. O. (1982), "Weed Control in Cowpea (*Vigna unguiculata*) in the Humid Tropics", Weed Science 30:331–334.
Bannon, J. S., Baker, J. B. and Rogers, R. L. (1978), "Germination of Wild Poinsettia (*Euphorbia heterophylla*)", Weed Science 26:221–225.
Harger, T. R. and Nester, P. R. (1980), "Wild Poinsettia: A Major Soybean Weed", Louisiana Agriculture 23(3):4–5,7.
Langston, V. B. and Harger, T. R. (1983), "Potential for Late Season Infestation by Wild Poinsettia", Pro. South. Weed Sci. Soc. 36:77.

*Primary Examiner*—Glennon H. Hollrah
*Assistant Examiner*—Amelia Owens
*Attorney, Agent, or Firm*—Roman Saliwanchik; David R. Saliwanchik

[57] ABSTRACT

The subject invention concerns a novel bioherbicide and its use to control major weeds found in many fields in the United States. Specifically, *Alternaria euphorbiicola* Simmons & Engelhard, having the identifying characteristics of deposit NRRL 18056, in an agricultural composition, can be used to effectively control wild poinsettia and weedy spurges. Further, *Alternaria euphorbiicola* Simmons & Engelhard, having the identifying characteristics of deposit NRRL 18056, in a mixture with *Alternaria cassiae* can be used to control wild poinsettia and weedy spurges and other undesired vegetation, such as sicklepod, showy crotalaria and coffee senna. Further, the bioherbicide of the invention can be mixed with a chemical herbicide to increase weed control.

6 Claims, No Drawings

BIOLOGICAL CONTROL OF WILD POINSETTIA AND OTHER WEEDY SPURGES WITH A FUNGAL PATHOGEN

BACKGROUND OF THE INVENTION

1. Field of the Invention

The instant invention is a method for the control of undesirable plants by use of plant pathogens.

2. Description of the Prior Art

The merits for using plant pathogens to control weeds in annual crops have been discussed previously for two Colletotrichum spp. (Daniel, et al. U.S. Pat. No. 3,849,104 and Templeton, U.S. Pat. No. 3,999,973). The anthracnose fungus Colletotrichum gloeosporioides has been used to control the weed northern jointvetch, and another strain of this fungus has been used to control winged waterprimrose. Colletotrichum malvarum has been used to control prickly sida. These three pathogens have been combined to control all three target weeds at once. In other work the fungus Alternaria cassiae (U.S. Pat. No. 4,390,360) has been used to control sicklepod, coffee senna, and showy crotalaria. Another fungus Fusarium lateritium (U.S. Pat. No. 4,419,120) has been used to control prickly sida, velvetleaf and spurred anoda. Included in this same patent, the synergistic interaction between F. lateritium and Alternaria macrospora has been used for control of spurred anoda.

Cercospora rodmanii has been used to control waterhyacinth (U.S. Pat. No. 4,097,261) and Phytophthora palmavora has been commercially developed as a biological herbicide for stranglervine.

Wild poinsettia (Euphorbia heterophylla L.) is a major weed problem in portions of the southern United States, Brazil, Columbia, Peru, Nigeria, and in several other countries which have tropical or subtropical climates (Akobundu, I.O. [1982] Weed Science 30: 331-334; Bannon, J. S., Baker, J. B. and Rogers, R. L. [1978] Weed Science 26: 221-225; Reed, C. F. [1977] U.S. Dept. Agric. Handbook No. 498). This annual species reduces yield through direct competition with crop plants and interferes with harvesting. The plants produce a sticky latex sap that interferes with harvesting and reduces seed quality of soybeans by increasing moisture levels and trash accumulation (Harger, T. R. and Nester, P. R. [1980] Louisiana Agric. 23(3): 4-5; Langston, V. B. and Harger, T. R. [1983] Proc. South. Weed Sci. Soc. 36: 77).

Wild poinsettia or "painted leaf" is an annual herb that commonly has two leaf shapes; long, narrow leaves, and wider, lobed leaves. Both leaf shapes can occur on the same plants. As plants mature, the foliage develops numerous dark spots (Bannon et al., supra).

Seed germination is greatly influenced by light and temperature. Seeds remain viable in soil for extended periods of time, and maximum germination rates occur as the soil temperatures increase in late spring and early summer (Bannon et al. and Harger et al., supra).

Wild poinsettia is difficult and expensive to control using conventional weed control practices. Planting soybeans early in the growing season before wild poinsettia seedlings emerge has been shown to provide some control. Chemical herbicides recommended for control of wild poinsettia include metribuzin, linuron, acifluorfen, and dinoseb. Multiple herbicide applications are often necessary for satisfactory control (Harger et al., supra).

Spotted spurge (*Euphoriba maculata* L.) is an annual species that is native to the eastern two-thirds of the United States. The leaves are oblong or lance-falcate, 0.8-3.5 cm long, with edges that are slightly toothed. A conspicuous reddish spot usually occurs at the base of each leaf. Spotted spurge is a major weed problem in soybeans, cotton, and other agronomic crops. Crop yields are reduced through direct competition. In addition, the milky sap present in the stems causes difficulty in harvesting.

Effective chemical control of spotted spurge is both difficult and expensive. Norflurazon is used in cotton, and in soybeans the herbicides used include acifluorfen, metribuzin, and dinoseb.

There is a need to have an effective means for the biological control of wild poinsettia and weedy spurges, for example, spotted spurge. Such a means would, advantageously, eliminate, or at least reduce the use of chemical agents to control these weeds. It is well known that the extensive use of chemicals to control weeds over the last twenty years has placed a heavy burden on the ecosystem, resulting in contamination of groundwater, lakes, rivers, etc. The substitution of biological control agents for many of these chemicals is recognized as a solution to this chemical contamination problem.

BRIEF SUMMARY OF THE INVENTION

The subject invention concerns the use of a novel isolate of the fungus *Alternaria euphorbiicola* Simmons & Engelhard to control the noxious weeds wild poinsettia and weedy spurges. Advantageously, this fungus controls these weeds when present among desired field crops without damaging the crops. For example, the novel *A. euphorbiicola* isolate of the invention can be used to control wild poinsettia found in a field planted with soybeans. Also, this novel isolate can be used to control spotted spurge present in fields of soybeans, cotton, and other agronomic crops. Though the prime use of the novel *A. euphorbiicola* isolate is to control wild poinsettia and weedy spurges in fields planted with desired crops, this fungus also can be used to control these weeds along roadways, river banks and lake shores, in recreational areas, and the like.

DETAILED DESCRIPTION OF THE INVENTION

The novel *A. euphorbiicola* isolate of the subject invention is the first known biological control agent for controlling wild poinsettia and weedy spurges. This novel *A. euphorbiicola* isolate, as a biologically pure culture, is on deposit with the Agricultural Research Culture Collection (NRRL) in Peoria, Ill., and has been assigned the accession number NRRL 18056. It was deposited on Mar. 12, 1986 to be maintained for 30 years. The address of the Curator of the Agricultural Research Culture Collection is: A. J. Lyons, Curator, ARS Patent Collection, Northern Regional Research Center, 1815 North University Street, Peoria, Ill. 61604.

According to E. G. Simmons, the description of the species is as follows:

"Conidia from 5-day-old colonies on PCA initially are long-ovid, enlarging to long-ellipsoid and producing as many as six transverse septa in a 60-70×18 μm sporebody before a longitudinal septum is formed in one of the central cells. Only one (rarely two) longitudinal or oblique septum is produced in 1-4 of the central transverse compartments of a conidium. Conidia lack a definable beak as an entity distinct from the spore-body. In culture, as in the type, the apical conidium cell readily lengthens and becomes converted into a functional conidiophore, a pseudorostrum; chains of as many as 4-5 or more units typically may be produced through this mechanism. Conidia appear to be smooth, pale tan, with well-defined transverse septa and poorly defined longitudinal ones of weak appearance." (Simmons, E. G. [1986] Mycotaxon 25(1): 195-202)

Following are examples which illustrate the process of the invention, including the best mode. These examples should not be construed as limiting. All solvent mixture proportions are by volume unless otherwise noted.

EXAMPLE 1

Inoculum Production

Inoculum of *A. euphorbiicola*, NRRL 18056, for tests was produced in petri dishes containing vegetable juice agar (V-8 juice, Campbell Soup Company) in accordance with the method of P. M. Miller disclosed in Phytopathology 45: 461-2 (1955) in an article entitled "V-8 juice agar as a general-purpose medium for fungi and bacteria." The cultures were incubated at 25° C. with a 12 hr diurnal light cycle supplied by two, 40-w cool white fluorescent bulbs that were suspended 20 cm above the cultures. The 12 hr dark cycle temperature was 19° C. To produce large quantities of inoculum, conidia from petri-dish-grown cultures were used to inoculate 500 ml of sterile liquid growth medium contained in cotton-plugged 1000 ml Erlenmeyer flasks. The liquid growth medium consisted of soyflour, 15 g/L; corn meal, 15 g/L; sucrose, 30 g/L; calcium carbonate, 3 g/L and distilled water.

The cultures were incubated at 25° C. on a rotary shaker at 160 rpm. After 4 to 5 days, the mycelial cultures were harvested and homogenized in a Waring Blendor for 30 sec. The mycelial homogenate was poured to a depth of 2 to 4 mm into shallow trays, and exposed to light from 250-w sunlamps for 5-15 min every 12 hr for 72 hr. The spores were vacuumed from the surface of the mycelial mat and stored at 4° C. This sporulation procedure has been described in H. L. Walker and J. A. Riley (1982) Weed Sci 30: 651-654.

Granular preparations containing mycelia and conidia were prepared using the sodium alginate process described by H. L. Walker and W. J. Connick, Jr. (1983) Weed Sci 31: 333-338.

Mycelial fragment preparations were prepared by growing the fungus in liquid growth medium consisting of soyflour, 45 g/L; corn meal, 30 g/L; soluble starch, 15 g/L; sucrose, 30 g/L; calcium carbonate, 3 g/L; and distilled water. The cultures were grown in Erlenmeyer flasks at 25° C. and 160 rpm. The mycelium was harvested 8 days after inoculation, and homogenized for 30 sec in a Waring Blendor. Kaolin clay (1% w/v) was added, and the mycelial-clay mixture was homogenized for 15 sec. The mixture was centrifuged 1460 xg for 10 min and the supernatant was decanted. The mycelium-clay pellet was placed on filter paper and dried for 5 to 7 days at 4° C. The dried cake was processed through a Wiley mill (Arthur H. Thomas Company, Philadelphia, PA) with a 20 mesh screen and the resulting preparation was stored at 4° C.

EXAMPLE 2

Host Range and Epidemiology

The plant species included in the greenhouse studies are listed in Table 1. Plants were grown in a commercial potting mix (Mix No. 2, Ball Seed Company, West Chicago, IL) in peat strips that contained 12 plants each. Temperatures ranged from 28° to 32° C. with 40 to 60% relative humidity. The day length was approximately 12 hr.

Plants in the cotyledon to third leaf stage of growth were sprayed to run off with inoculum applied with an atomizer. Inoculation mixtures contained 0.02% (v/v) surfactant, nonoxynol (9 to 10 PEO) [a(p-nonylphenyl)-w-hydroxypoly(oxyethylene)] in distilled water and $1 \times 10^5$ spores/ml. Control plants were sprayed with water and 0.02% surfactant only. All plants were placed in dew chambers for 20 hr at 25° C. The plants then were moved to greenhouse benches and evaluated daily for 14 days. All tests were repeated on at least two dates, and 12 plants were used for each treatment in each test.

The fungus was pathogenic and highly virulent to wild poinsettia seedlings. Most seedlings in the cotyledon to fourth leaf stage of growth were killed 2 to 7 days affer inoculation. The pathogen produced dark brown to black lesions 1-5 mm in diam on the leaves and stems within 2 days. The lesions enlarged with time on any remaining plants and produced severe stem canker and defoliation within seven days. Several other weedy spurge species appeared to be as susceptible as wild poinsettia to the pathogen. Other representative crop and weed species were resistant to the pathogen; however, phytotoxic damage was occasionally observed on inoculated leaves of several species (Table 1). Phytotoxic symptoms ranged from flecking to a marginal or interveinal "burn" of inoculated leaves. These symptoms appeared within 48 to 72 hr after inoculation and did not increase in number or severity with time. Succulent tissues were most susceptible to damage. The phytotoxicity is attributed to the high concentrations of conidia contained in the inoculation mixtures. Phytotoxic injury was not observed in every test and this injury was never observed on the control plants.

Wild poinsettia plants in all stages of growth were infected by the fungus; however, plants in the fourth leaf growth stage and younger were most severely damaged (Table 2).

The fungus infected plants within a dew period temperature range of 10° to 35° C. (Table 3). At 25° C., the fungus infected with dew periods ranging from 0 to 24 hr (Table 4), and inoculum levels of 10,000 to 500,000 spores per ml (Table 5).

This foliar pathogen can be formulated and applied to the target weeds as a spray (wettable powder) or as granules that consist of the fungus and a carrier such as vermiculite, corn cob grits, or clay. Advantageously, preemergence or postemergence applications of granules can be used. The granular formulation of a foliar pathogen for soil application for preemergence weed control is unexpected because soil-inhabiting organisms compete with the pathogen.

The preferred liquid carrier is water, and the spore concentrate is dispersed to make a concentration of from about $1 \times 10^4$ to about $1 \times 10^6$ spores/ml.

Spores of *A. euphorbiicola* can be mixed with those of *Alternaria cassiae* to enlarge the scope of control of undesirable vegetation. For example, this mixture can be used to control both wild poinsettia and sicklepod (*Cassia obtusifolia*), two troublesome weeds in the Southeast. Further, spores of *A. euphorbiicola* can be mixed with those of *A. cassiae* to control wild poinsettia and coffee senna. The use of *A. cassiae* to control sicklepod, showy crotalaria and coffee senna is disclosed in U.S. Pat. No. 4,390,360, which is incorporated herein by reference thereto. The culture, means of growing, and application to these weeds disclosed in U.S. Pat. No. 4,390,360 can be used herein. Mixtures of *A. euphorbiicola* and *A. cassiae*, for example, *A. cassiae* NRRL 12533, can be made by methods well known in the art, utilizing the disclosure of U.S. Pat. No. 4,390,360 and that contained herein.

Though spores are the preferred form of the fungi, the fungi also can be formulated as fragmented mycelia and applied as foliar sprays.

Spores or mycelial fragments of *A. euphorbiicola* can be combined with various chemical additives, particularly chemical herbicides, to increase weed control. These additives would be expected to broaden the spectrum of activity so that additional species of weeds can be controlled. Application rates of these chemicals would be expected to be less than or equal to the rates recommended for conventional use.

Examples of these chemicals include but are not limited to the following:

| Trade Name[1] | Chemical Name | Common Name |
|---|---|---|
| Alanap (B) | 2-[(1-naphthalenylamino)carbonyl] berzoic acid | naptalam |
| Basagran (B) | Sodium salt of (3-isopropyl-1 H—2,1,3-bentzothiadiazin-4 (3H)—one 2,2-dioxide) | bentazon sodium salt |
| Basta (B & G) | Ammonium-DL-homoalanin-4-yl (methyl) phosphinate | glufosinate ammonium |
| Blazer (B & G) | Sodium 5-[2-chloro-4-trifluoro methyl)phenoxy]-2-nitrobenzoate | acifluorfen sodium salt |
| Butyrac 200 (B) | 4-(2,4-Dichlorophenoxy)butyric acid | 2,4-DB |
| Cobra (B) | 1-(carboethoxy)ethyl 5-[2-chloro-4-(trifluoromethyl)phenoxy]-2-nitrobenzoate | lactofen |
| DOWPON (G) | 2,2'-dichloropropionic acid | dalapon |
| Fusilade (G) | Butyl(R—S)-2-[4-[[5-(trifluoromethyl)-2-pyridinyl]oxy]phenoxy] propanoate | fluazifop |
| Hoelon (G) | Methyl 2-[4-(2,4-dichlorophenoxy) phenoxy]propanoate | diclofop methyl |
| Premerge 3 (B & G) | Dinoseb(2-sec-butyl-4,6-dinitrophenol) as the alkanolamine salts | dinoseb |
| Roundup (B & G) | Isopropylamine salt of N—(phosphonomethyl)glycine | glyphosate |
| Scepter (B) | Ammonium salt of 2-[4,5-Dihydro-4-methyl ethyl)-5-oxo-1H—imidazol-2-yl]-3-quinoline carboxylic acid | imazaquin |
| Classic | 2-(([(4-chloro-6-methoxpyrimidine-2-yl)amino carbonyl] amino sulfonyl))benzoic acid ethyl ester | DPX-F6025 |
| Dual 8E | 2-chloro-N—(2-ethyl-6-methylphenyl)-N—(2-methoxy-1-methylethyl)acetamide | metolachlor |
| Poast | 2-[1-(ethoxyimino)butyl]-5[2-(ethylthio)propyl]-3-hydroxy-2-cyclohexen-1 one | sethoxydim |
| Sencor | 4-Amino-6-(1,1-dimethylethyl)-3-(methylthio)-1,2,4,-triazin-5(4H)—one | metribuzin |
| Lorox, Linurex | 3-(3,4-dichlorophenyl)-1-methoxy-1-methylurea | linuron |
| Karmex | 3-(3,4-dichlorophenyl)-1,1-dimethylurea | diuron |
| Surflan | 3 5-Dinitro-$N^4N^4$—dipropyl-sulfanilamide | oryzalin |
| B-Nine | Daminozide butanedioic acid mono(2,2-dimethylhydrazide) | Alar |
| Dropp | N—phenyl-N'—1,2,3-thiadiazol-5 yl urea | thidiazuron |
| Embark | Diethanolamine salt of (N—[2,4-dimethyl-5-[[(trifluoromethyl)-sulfonyl]amino]phenyl]acetamide | mefluidide |
| Stik | 1-Naphthaleneacetic acid | NAA |

[1]The notation in parentheses indicates the activity of the herbicide (B = broadleaf control, G = grass control, and B & G = broadleaf and grass control.

TABLE 1

Reaction of Various Plant Species to *Alternaria euphorbiicola*[a]

| Family Species | Defoliation | Plants with stem lesions | Disease Rating[b] |
|---|---|---|---|
| Cruciferae | | | |
| Turnip (*Brassica rapa*) 'Purple Top' | 0 | 0 | R |
| Cucurbitaceae | | | |
| Watermelon (*Citrullus vulgaris*) 'Charleston Grey' | 0 | 0 | R |
| Euphorbiaceae | | | |
| Poinsettia (*Euphorbia pulcherrima*) Christmas Poinsettia | 0 | 0 | S |
| Poinsettia (*Euphorbia heterophylla*) Mexican Fire Plant | <10% | >95% | S |
| Poinsettia (*Euphorbia heterophylla*) Wild Poinsettia | >85% | >95% | S |
| Spurge (*Euphorbia hyssopifolia*) | >85% | >95% | S |
| Spurge (*Euphorbia polychroma*) | 0 | 0 | S |
| Spurge (*Euphorbia supina*) Prostrate Spurge | >85% | >95% | S |
| Leguminosae | | | |
| Beggarweed (*Desmodium tortuosum*) Florida Beggarweed | 0 | 0 | R+ |
| Lima bean (*Phaseolus limensis*) 'Jackson Wonder' | 0 | 0 | R |
| Cowpea (*Vigna sinensis*) 'California Pinkeye' | 0 | 0 | R |
| Sicklepod (*Cassia obtusifolia*) | 0 | 0 | R+ |
| Soybean (*Glycine max*) | | | |
| 'Forrest' | 0 | 0 | R |
| 'Hill' | 0 | 0 | R |
| Malvaceae | | | |
| Cotton (*Gossypium hirsutum*) | | | |
| 'DPL-61' | 0 | 0 | R+ |
| 'Stoneville 50' | 0 | 0 | R+ |
| Okra (*Abelmoschus esculentus*) 'Clemson Spineless' | 0 | 0 | R+ |
| Prickly sida (*Sida spinosa*) | 0 | 0 | R+ |
| Velvetleaf (*Abutilon theophrasti*) | 0 | 0 | R |
| Solanaceae | | | |
| Tomato (*Lycopersicon esculentum*) | | | |
| 'Better Boy' | 0 | 0 | R |
| 'Manalucie' | 0 | 0 | R |
| 'Rutgers' | 0 | 0 | R |

[a]Plants of each species were sprayed with inoculum containing $1 \times 10^5$ spores/ml. Data were collected 14 days after inoculation.
[b]R = resistant and S = susceptible to the pathogen; + = phytotoxic injury by the pathogen limited to flecking or small, nondamaging burning of the leaves.

TABLE 2

Effect of Growth Stage on Control of Wild Poinsettia by *Alternaria euphorbiicola*[a]

| Growth Stage | Plants Killed (%) |
|---|---|
| Cotyledon | 33 |

TABLE 2-continued

Effect of Growth Stage on Control of Wild Poinsettia by *Alternaria euphorbiicola*[a]

| Growth Stage | Plants Killed (%) |
|---|---|
| 1 Leaf | 83 |
| 2 Leaves | 100 |
| 3 Leaves | 50 |
| 4 Leaves | 83 |
| 5 Leaves | 17 |

[a]Twelve plants at each growth stage were sprayed to wetness with a suspension containing $1 \times 10^5$ conidia/ml. Plants received a 20-hr dew period at 25° C. Data were collected 14 days after inoculation.

TABLE 3

Effect of Different Dew-Period Temperatures on the Control of Wild Poinsettia by *Alternaria euphorbiicola*

| Temperature (C.) | Plants Killed (%) |
|---|---|
| 10 | 67 |
| 15 | 50 |
| 20 | 83 |
| 25 | 92 |
| 30 | 8 |
| 35 | 17 |

[a]Twelve plants in the first to second-leaf state were sprayed to wetness with a suspension containing $1 \times 10^5$ conidia/ml; dew-periods were 20 hr. Data were collected 14 days after inoculation.

TABLE 4

Effect of Dew-Period Duration on the Control of Wild Poinsettia by *Alternaria euphorbiicola*[a]

| Length of Dew-Period (hr) | Plants Killed (%) |
|---|---|
| 0 | 17 |
| 4 | 58 |
| 8 | 58 |
| 12 | 75 |
| 16 | 83 |
| 20 | 100 |
| 24 | 92 |

[a]Twelve plants in the first to second leaf stage of growth were sprayed to wetness with a suspension that contained $1 \times 10^5$ conidia/ml, then placed in dew chambers at 25° C. Data were collected 14 days after inoculation.

TABLE 5

Effect of Inoculum Levels on the Control of Wild Poinsettia with *Alternaria euphorbiicola*[a]

| Spore Concentration (No./ml, $\times 10^4$) | Plants Killed (%) |
|---|---|
| 0 | 0 |
| 1 | 33 |
| 5 | 75 |
| 10 | 92 |
| 50 | 100 |

[a]Twelve plants in the first to second-leaf stage were inoculated with each spore concentration. Dew-periods were 20 hr at 25° C. Data were collected 14 days after inoculation.

What is claimed is:

1. A composition for controlling wild poinsettia and weedy spurges comprising a herbicidally effective amount of novel isolate of the fungus *Alternaria euphorbiicola*, having the identifying characteristics of deposit NRRL 18056, in association with an inert agricultural carrier.

2. A composition, according to claim 1, wherein said *Alternaria euphorbiicola*, having the identifying characteristics of deposit NRRL 18056, is in the spore form at a spore concentration of from about $1 \times 10^4$ spores/ml of carrier to about $1 \times 10^6$ spores/ml of carrier.

3. A process for controlling wild poinsettia or weedy spurges which comprises applying a herbicidally effective amount of the fungus *Alternaria euphorbiicola*, having the identifying characteristics of deposit NRRL 18056, onto said wild poinsettia or weedy spurges or unto the situs of said wild poinsettia or weedy spurges.

4. A process, according to claim 3, wherein said weedy spurge is spotted spurge.

5. A biologically pure culture of a novel isolate of *Alternaria euphorbiicola*, having the identifying characteristics of deposit NRRL 18056, and having the novel properties of pathogenicity to wild poinsettia and weedy spurges.

6. A process for controlling wild poinsettia which comprises applying a herbicidally effective amount of the fungus *Alternaria euphorbiicola*, having the identifying characteristics of deposit NRRL 18056, onto said wild poinsettia or unto the situs of said wild poinsettia.

* * * * *

UNITED STATES PATENT AND TRADEMARK OFFICE
CERTIFICATE OF CORRECTION

PATENT NO. : 4,755,208

DATED : July 5, 1988

INVENTOR(S) : Joe A. Riley, Harrell L. Walker

It is certified that error appears in the above-identified patent and that said Letters Patent is hereby corrected as shown below:

Table 1, Col. 6:   line 51:   "'Stoneville 50'" should read --'Stoneville 506'--.

Signed and Sealed this

Twenty-third Day of April, 1991

Attest:

HARRY F. MANBECK, JR.

*Attesting Officer*   *Commissioner of Patents and Trademarks*